United States Patent [19]
Powers

[11] Patent Number: 5,211,370
[45] Date of Patent: May 18, 1993

[54] VARIABLE ORIFICE SEALING VALVE

[76] Inventor: Ronald J. Powers, 4010 Ischia Dr., Oxnard, Calif. 93035

[21] Appl. No.: 817,390

[22] Filed: Jan. 6, 1992

[51] Int. Cl.⁵ ............................................. F16K 7/08
[52] U.S. Cl. ................................... 251/4; 251/212
[58] Field of Search ................................ 251/4, 212

[56] References Cited

U.S. PATENT DOCUMENTS

| | | | |
|---|---|---|---|
| 1,986,484 | 1/1935 | Schlueter | 251/4 X |
| 3,329,390 | 7/1967 | Hulsey | 251/4 |
| 3,366,363 | 1/1968 | Hogan et al. | 251/4 |
| 4,292,969 | 10/1981 | Raible | 251/4 |
| 4,540,411 | 9/1985 | Bodicky | 251/4 X |

Primary Examiner—John C. Fox
Attorney, Agent, or Firm—Edgar W. Averill, Jr.

[57] ABSTRACT

A variable orifice sealing valve made from a thin, elastic cylinder. The cylinder is retained at both ends, and one end is twisted with respect to the other end thereby reducing the fluid flow path through the center of the cylinder. The device is particularly useful for medical procedures such as in conjunction with a catheter.

10 Claims, 2 Drawing Sheets

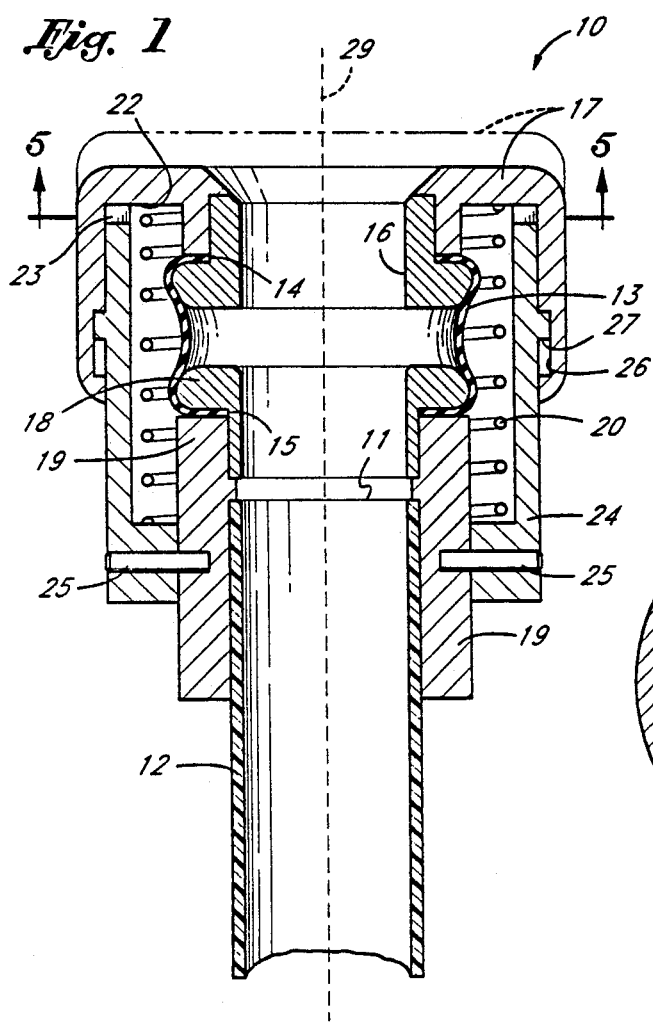
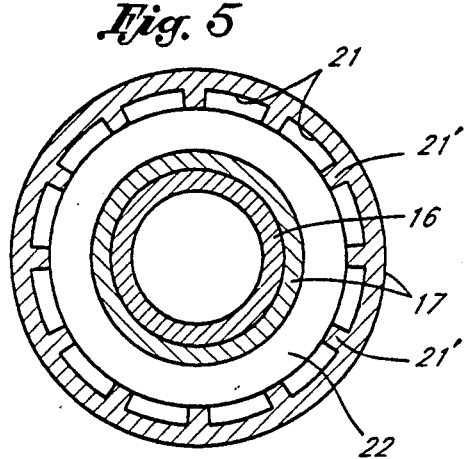
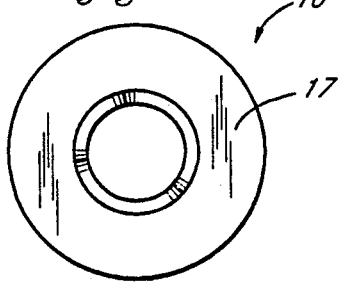
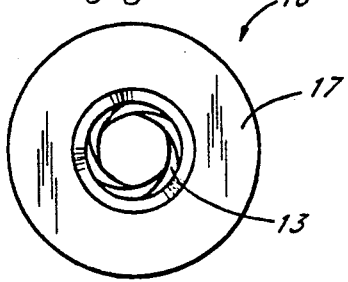
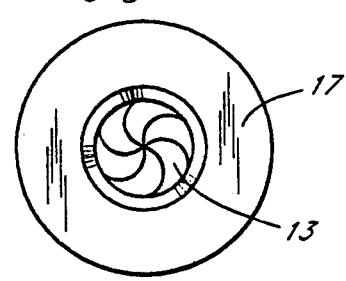

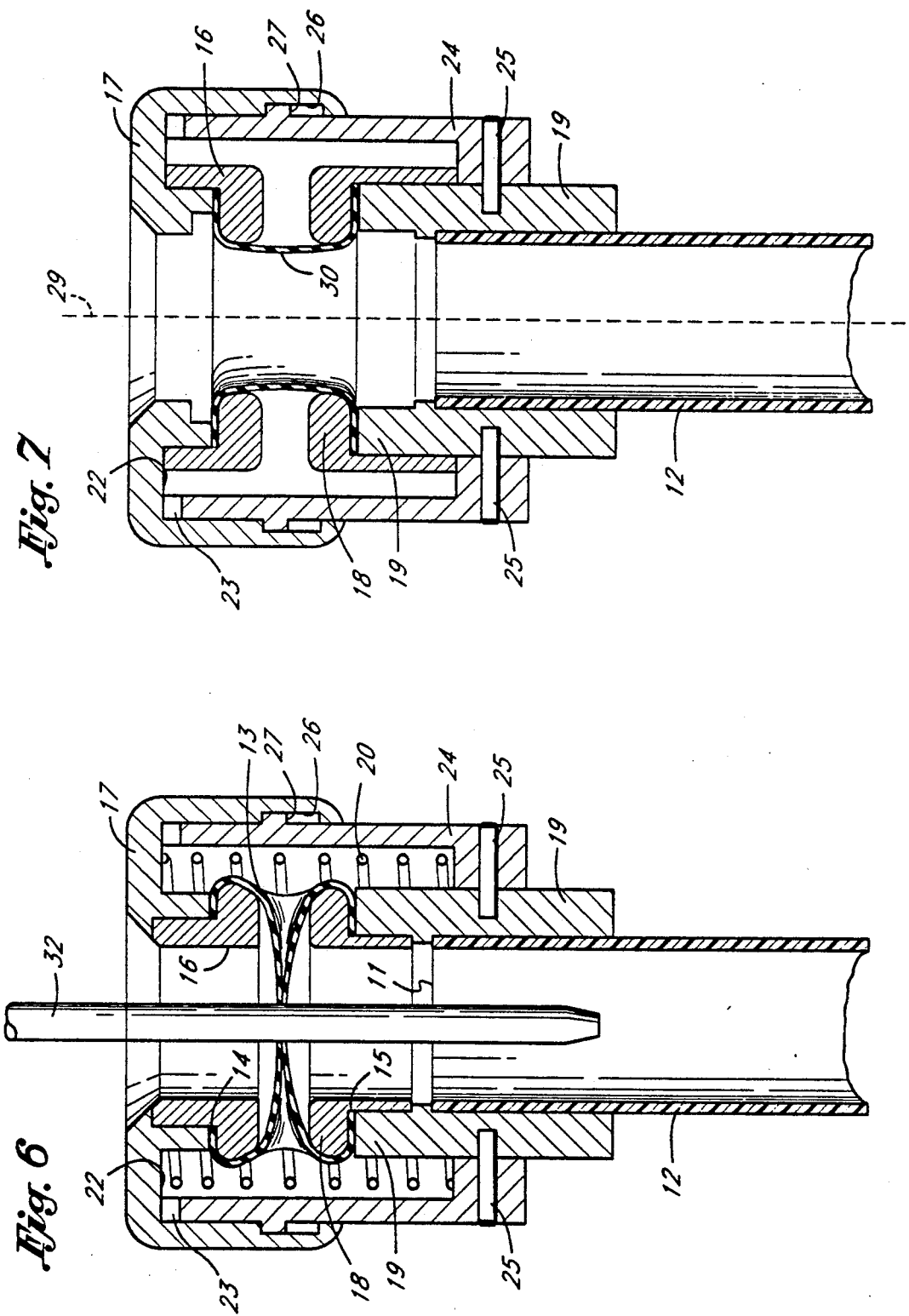

VARIABLE ORIFICE SEALING VALVE

BACKGROUND OF THE INVENTION

The field of the invention is fluid flow controlling devices, and the invention relates more particularly to fluid flowing devices in medical applications where it is desired to seal a catheter or other instrument in a manner which permits the instrument to be passed through the valve, and the valve forms a seal against the walls of the instrument.

Various valve designs have been utilized such as those shown in the following U.S. Pat. Nos.: 4,430,081; 4,693,257; 4,798,594; 4,857,062; 4,917,668; 4,978,341; 5,009,391 and 5,059,186. Most of these devices utilize a rubber disk or cylinder having a slit formed therethrough wherein the medical device either cuts or spreads the size of the opening. Such procedures either form an imperfect seal or provide too much resistance so that the feel, or control, of the instrument is adversely affected.

For many operations, it is desired to have a valve which may be opened or closed and controlled in size. In that way, additional procedures not heretofore believed possible can be carried out which require an opening and closing of a valve which may still be closed about the periphery of the instrument.

SUMMARY OF THE INVENTION

It is an object of the present invention to provide a valve which is controllable in size, centered within an orifice and flexible so that it may be sealed against an instrument or other object inserted therethrough.

The present invention is for a variable orifice sealing valve having a thin, elastic cylinder with a first end and a second end and a cylindrical length. A first ring member is affixed at one end of the thin, elastic cylinder, and a second ring member is affixed to the second end of the cylinder. When one ring is turned with respect to the other ring, the elastic cylinder tends to close down against the central area forming an infinitely controllable opening which may be reduced to a completely closed area. The fluid flow through the valve is limited to the middle of the valve. There is not the usual valve seal problems which exist between a valve and the control stem thereof since there is no control stem.

The present invention also includes a method for controlling the flow of fluid comprising passing fluid through an elastic cylinder and turning one end of the cylinder with respect to the other end thereby reducing the fluid flow area through the elastic cylinder.

BRIEF DESCRIPTION OF THE DRAWINGS

FIG. 1 is a cross-sectional side view of the variable orifice sealing valve of the present invention affixed at the end of an open tube.

FIG. 2 is a top plan view thereof showing the valve in completely open configuration.

FIG. 3 is a plan view thereof showing the valve partially closed.

FIG. 4 is a plan view thereof showing the valve completely closed.

FIG. 5 is a cross-sectional view taken along line 5—5 of FIG. 1.

FIG. 6 is a cross-sectional view analogous to FIG. 1 except showing the valve in a partially closed configuration.

FIG. 7 is a cross-sectional side view of an alternate embodiment of the variable orifice sealing valve of the present invention.

DESCRIPTION OF THE PREFERRED EMBODIMENTS

A variable orifice sealing valve is shown in cross-sectional side view in FIG. 1 and identified generally by reference character 10. Valve 10 is affixed at the open end 11 of a tube 12. The valve comprises a thin, elastic cylinder 13 having a first end 14 and a second end 15. Cylinder 13 is held in a pair of holding rings comprising a first ring having an inner member 16 and an outer member 17 which holds the first end of cylinder 13. A second ring assembly having an inner member 18 and an outer member 19 holds the second end 15 of cylinder 13. A torsion spring 20 is affixed between the outer members 17 and 19 and tends to force the thin, elastic cylinder 13 into a closed configuration as shown in FIG. 4. The valve is held in a desired position by the meshing of a series of recesses 21 and teeth 21' on the undersurface 22 of outer member 17 with a series of teeth 23 on the upper surface of a collar 24 affixed by pins 25 to outer member 19. A recess 26 captures a ring stop 27 which permits outer member 17 to be slightly lifted so that teeth 23 do not mesh with teeth 21'.

In operation, outer member 17 is lifted so that the teeth 23 no longer mesh with recesses 21, and the valve is turned thereby urging the elastic cylinder 13 into a twisted configuration as shown in FIG. 3. As the ring is further turned, the cylinder forms a completely closed configuration as shown in FIG. 4 of the drawings. The partially closed valve is shown in side view in FIG. 6 so that the twisting and closing action is seen from a side view.

It can be readily understood that a catheter 32, or other instrument, can be inserted into tube 12 through the center of thin, elastic cylinder 13, and then the outer member 17 twisted so that the thin, elastic cylinder closes down around the instrument. Furthermore, even when the valve is in a closed configuration, as shown in FIG. 4, an instrument still may be inserted through the center since the elastic cylinder 13 is deformable. Still further, the elastic cylinder tends to center the instrument in the tube and can be retained in a partially closed configuration, as shown in FIG. 3 of the drawings, so that it provides a minimum of resistance against movement of the instrument while still sealing the instrument against fluid flow around the instrument.

An alternate configuration of the variable orifice sealing valve of the present invention is shown in FIG. 7 where elastic cylinder 30 is shown on the inner surface of the device. Also, FIG. 7 is shown without a torsion spring since this is not essential to the operation of the device.

Thus in use, the flow of fluid is controlled by directing the same through the center of an elastic cylinder which has a ring at each end. When the ring at one end is twisted with respect to the ring at the other end, the passageway closes down. The rings and cylinder all have a longitudinal central axis indicated by reference character 29 in FIG. 1.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. A variable orifice sealing valve comprising:
    a thin, elastic cylinder having a first end, a second end and a cylindrical length and when at rest having a central opening comprising a fluid passageway therethrough having a passageway area;
    a first ring member affixed to the first end of said thin, elastic cylinder in a manner so that the first ring member will not turn with respect to said first end;
    a second ring member affixed to the second end of said thin, elastic cylinder in a manner so that the second ring member will not turn with respect to said second end, whereby when said first ring is turned with respect to said second ring, the fluid passageway will change in area; and
    a spring mounted exteriorally of said thin, elastic cylinder, said spring having a first end and a second end, said first end being affixed to said first ring member and said second end being affixed to said second ring member, said spring urging the first ring to turn with respect to the second ring.

2. A variable orifice sealing valve for controlling the flow of fluid therethrough, said valve comprising:
    a length of flexible tubing having a central axis, a first end and a second end;
    a first ring, having a central axis, affixed to said length of flexible tubing inwardly from the first end so that its central axis is generally parallel to the central axis of said length of flexible tubing;
    a second ring, having a central axis, affixed to said length of flexible tubing inwardly from the second end so that its axis is generally parallel to the central axis of the length of flexible tubing;
    means for turning the first ring about its central axis with respect to the second ring; and
    a spring mounted exteriorally of said length of flexible tubing, said spring having a first end and a second end, said first end being affixed to said first ring and said second end being affixed to said second ring, said spring urging the first ring to turn with respect to the second ring.

3. A valve positioned within a tube, which valve is capable of having an object centrally inserted therethrough in a leakproof manner comprising:
    an elongated tube having an open end, said elongated tube having a longitudinal axis;
    an elastic cylinder having a first end and a second end and a longitudinal axis and having an open area normal to its longitudinal axis, said second end of said elastic cylinder being affixed about the open end of said elongated tube so that the longitudinal axis of said elastic cylinder is about parallel to the longitudinal axis of said elongated tube;
    an outer ring member having a central axis, said outer ring member being affixed to the first end of said elastic cylinder so that its central axis is about parallel to the longitudinal axis of said elastic cylinder, said outer ring member including means for turning the outer ring about its central axis with respect to the elongated tube whereby when the outer ring member is turned, the inner area of said elastic cylinder is reduced or eliminated and elastically forced against any object inserted therethrough; and
    torsion means to urge the outer ring member to turn with respect to the elongated tube.

4. The valve of claim 3 wherein said outer ring member includes ratchet means to hold said outer ring member in a preferred position.

5. The valve of claim 3 wherein said torsion means urges the outer ring member into a twisted configuration so that the valve will tend to more to a closed position.

6. The valve of claim 3 further including an outer ring supporting collar affixed near the open end of said elongated tube, said collar including a cylindrical portion extending away from the open end of said elongated tube, and said outer ring member including a collar including a cylindrical portion extending over said cylindrical portion of said outer ring supporting collar.

7. The valve of claim 6 wherein outer ring supporting collar is spaced apart from the elongated tube and the elastic cylinder to provide a torsion spring space and further including torsion spring means affixed at one end to the elongated tube and at the other end to the outer ring.

8. The valve of claim 7 further including ratchet means between said outer ring member and said outer ring supporting collar.

9. The valve of claim 8 wherein said ratchet means comprises a first set of gear teeth on said outer ring supporting collar and a second set of gear teeth which mesh with the first set of gear teeth held by said outer ring member and means for engaging and disengaging the first and second gear teeth.

10. The valve of claim 9 wherein said means for engaging and disengaging said first and second gear teeth comprises moving the outer ring member outwardly with respect to the outer ring supporting collar.

* * * * *